(12) United States Patent
Bejan et al.

(10) Patent No.: US 7,851,619 B2
(45) Date of Patent: Dec. 14, 2010

(54) PROCESS FOR THE PREPARATION AND PURIFICATION OF EPLERENONE

(75) Inventors: Elena Bejan, Brantford (CA); Bhaskar Reddy Guntoori, Brantford (CA); Svetoslav S. Bratovanov, Ancaster (CA); Mohamed Ibrahim Zaki, Brantford (CA); Stephen E. Horne, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 903 days.

(21) Appl. No.: 11/727,421

(22) Filed: Mar. 26, 2007

(65) Prior Publication Data

US 2008/0234478 A1  Sep. 25, 2008

(30) Foreign Application Priority Data

Mar. 20, 2007 (CA) .................................. 2582496

(51) Int. Cl.
*C07J 71/00* (2006.01)
(52) U.S. Cl. ........................................................ 540/25
(58) Field of Classification Search ................... 540/25
See application file for complete search history.

(56) References Cited

U.S. PATENT DOCUMENTS 4,559,332 A  12/1985  Grob et al.
6,887,991 B1  5/2005  Ng et al.

FOREIGN PATENT DOCUMENTS

WO  WO 01/42272 A3  6/2001

OTHER PUBLICATIONS

Rabasseda, et al., Drugs of the Future, (1999), 24(5), pp. 488-501.
Grob, et al., Helvetica Chimica Acta, (1997), vol. 80, pp. 566-585.

*Primary Examiner*—Barbara P Badio

(57) ABSTRACT

A process for the preparation and purification of Eplerenone is described wherein hydroxylated impurities are removed using a novel derivatization procedure.

21 Claims, No Drawings

PROCESS FOR THE PREPARATION AND PURIFICATION OF EPLERENONE

FIELD OF THE INVENTION

The present invention describes a new process for the preparation and purification of Eplerenone.

BACKGROUND OF THE INVENTION

Eplerenone, (7α,11α,17α)-9,11-epoxy-17-hydroxy-3-oxo-pregn-4-ene-7,21-dicarboxylic acid, γ-lactone, 7-methyl ester, is a mineralocorticoid receptor antagonist useful in the treatment of high blood pressure and congestive heart failure. It is marketed under the name of INSPRA™.

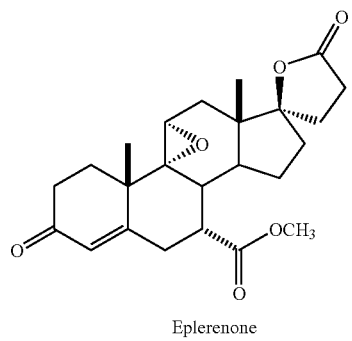

Eplerenone

Most of the patents and literature information dealing with the preparation of Eplerenone are based on the use of the known trienone I as a starting material. In turn, the trienone I is obtained from the natural product Canrenone by 11-biohydroxylation followed by mesylation and elimination. The trienone I is then treated with diethylaluminum cyanide to form the 7-cyano derivative II that, after a reduction/oxidation sequence, yields intermediate III.

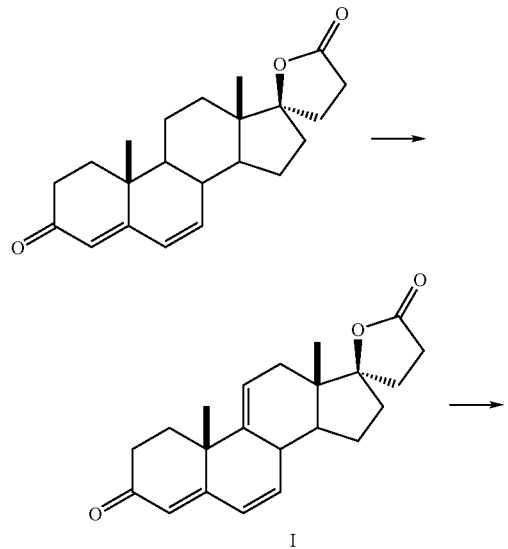

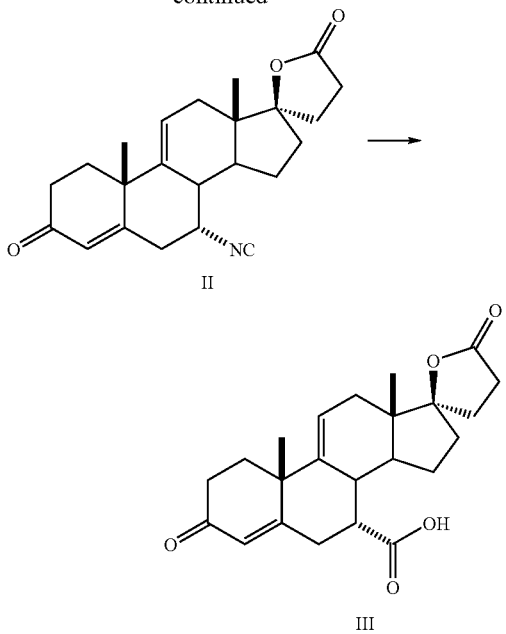

Crude intermediate III is reacted with diazomethane to provide the methyl ester intermediate IV which is then epoxidized using hydrogen peroxide in the presence of an initiator to yield Eplerenone.

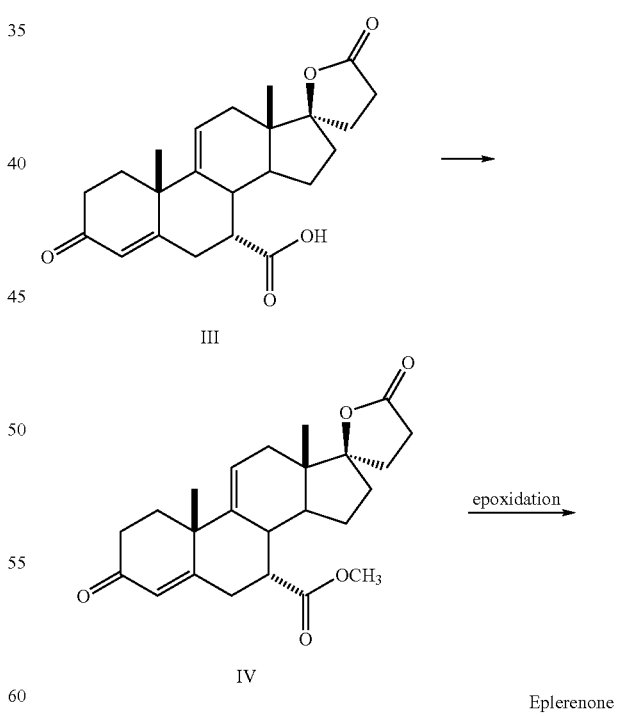

The original patent, U.S. Pat. No. 4,559,332, for the preparation of Eplerenone describes the epoxidation reaction of IV using hydrogen peroxide in the presence of trichloroacetonitrile as initiator. This patent does not disclose any information with respect to the purity of the material obtained, its purification, or the removal of impurities.

When the present inventors repeated the preparation taught in U.S. Pat. No. 4,559,332, it was observed that the purity of the resulting Eplerenone was low (70%) and attempts to purify the resulting product to a level meeting the requisite specifications for use as a pharmaceutical active were unsuccessful [typically, known impurities cannot be >0.2% (w/w)]. In particular, dihydroxylated compounds V and VI, which were isolated and identified, were very difficult to remove. Noteworthy is that similar compounds were mentioned elsewhere in the literature (U.S. Pat. No. 6,887,991), although methods for their removal were not disclosed.

V

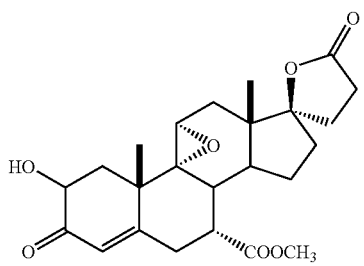

VI

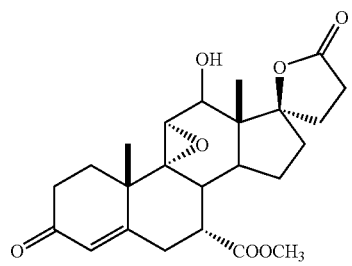

Other patent literature on processes for the synthesis of Eplerenone, for instance WO2001/042272, discloses examples for the purification of Eplerenone by recrystallization; however, the main objective of these patents was the preparation of various polymorphic and solvated forms. Again, even after numerous attempts to remove the dihydroxylated impurities V and VI from crude Eplerenone by recrystallization using these solvents and solvent mixtures, we were unable to obtain satisfactory purities of finished pharmaceutical active.

Therefore, an industrially acceptable method to prepare and purify Eplerenone was required.

SUMMARY OF THE INVENTION

Surprisingly, we have discovered a novel process for the preparation of Eplerenone which is based on the reaction of trienone IV with hydrogen peroxide in the presence of an initiator followed by the purification of the crude material by converting the compounds V and VI into their corresponding protected alcohols (VII and VIII wherein R=C(O)R' or S(O)$_2$R'', more preferably R=C(O)CH$_3$ or S(O)$_2$CH$_3$) and precipitation of Eplerenone from the reaction mixture. It could optionally be further purified by subsequent recrystallization.

VII

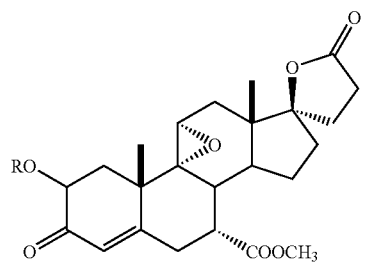

VIII

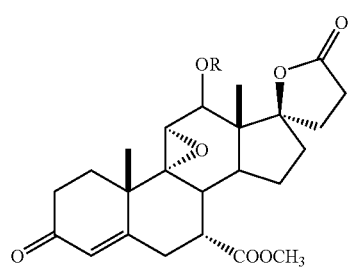

This new method of purification by derivatization was extensively studied using various reagents, bases and solvents. The most preferred results were obtained by treatment of the reaction mixture with acetic anhydride and triethylamine, followed by recrystallization. This novel method of derivatization of the impurities present in crude Eplerenone allowed removal of the corresponding acetylated derivatives VII and VIII (wherein R=C(O)CH$_3$) by recrystallization in a single solvent.

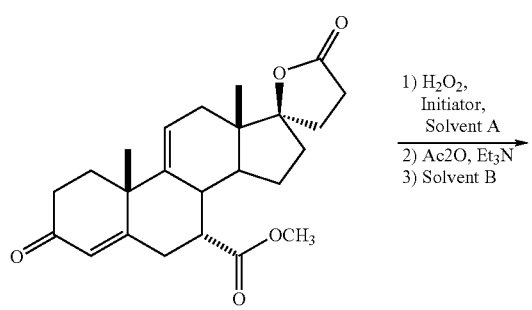

IV

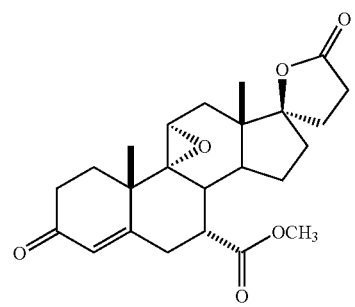

Eplerenone

According to one embodiment of the present invention there is provided a new and improved three step, one-pot process for the preparation and purification of Eplerenone.

This process is robust and amenable to scale-up to industrial levels.

Other advantages of the present invention include the improved cost efficiency and simplicity of the process. As well, the Eplerenone produced meets purity specifications of >99% with all known impurities being <0.2% (w/w).

Further and other advantages of this invention will be appreciated by those skilled in the art.

This method of purification has not been reported previously for the preparation of Eplerenone, to our understanding.

DESCRIPTION OF A PREFERRED EMBODIMENT

The hydrogen peroxide-mediated epoxidation of IV to crude Eplerenone was achieved by dissolution in an organic solvent, most preferably a C1-C3 chlorinated organic solvent, for instance dichloromethane followed by the addition of an initiator and a base. Examples of the initiator include trichloroacetonitrile and examples of the base include potassium hydrogenphosphate dibasic. Aqueous hydrogen peroxide is then added and the reaction is performed between 10 and 40° C. and further processed using standard aqueous extractive techniques.

The reaction mixture is then derivatized using a derivatizing agent in combination with an organic amine base such as triethylamine. Examples of the derivatizing agent include anhydrides of formula $[R'OC(O)]_2$ or $[R'OC(O)]_2$ and activated carboxylates of formula $R'C(O)X$ wherein X is a leaving group such as a halogen, most preferably X is chlorine. R' can be C1 to C6 alkyl, aryl or aralkyl, most preferably, R' is methyl. In another embodiment, the derivatizing agent can be sulfonate-ester forming agents of formula $R''S(O)_2X$ wherein R'' is C1 to C6 alkyl or aryl, most preferably R'' is methyl and X is as defined above.

The most preferred derivatizing agents for this invention are acetylating and sulfonating agents, such as acetic anhydride and acetyl chloride or sulfonates such as methanesulfonyl chloride. This reaction is preferably carried out at about 5° C. to about 50° C., most preferably at reflux temperature. The amount of organic base and derivatizing reagent should be sufficient to effect conversion of V and VI to their respective acetates or sulfonates, for instance about 0.1 to about 1.0 equivalents based on the original amount of III. Eplerenone is then optionally further purified by recrystallization from suitable organic solvents, for instance C3-C6 ketones, most preferably methyl ethyl ketone.

The following examples are representative of embodiments of the present invention and are not intended to be limiting.

Example 1

Preparation of Crude Eplerenone

A mixture of 7-α-(methoxycarbonyl)-3-oxo-17-α-pregna-4,9(11)-diene-21,17-carbolactone (100 g, 0.25 mol.), (48.8 g, 0.29 mol.), trichloroacetonitrile (91.0 g, 0.63 mol.) in dichloromethane (1000 mL) was stirred at reflux for 1 hour. Hydrogen peroxide 30% (398.4 g, 3.51 mol.) was added over 3 to 5 hours. The reaction mixture was stirred at reflux for 24 hours. After cooling to room temperature, the organic phase was washed twice with sodium sulfite 10% aqueous solution (2×400 g) followed by water (500 g). The solution was tested for peroxides and, when the test was negative, it was evaporated to 200 mL. If the test was positive, the aqueous sodium sulfite and water washes were repeated and the solution was retested.

Example 2

Preparation of Pure Eplerenone

The above organic phase was treated with triethylamine (12.7 g, 0.13 mol.) and acetic anhydride (12.8 g, 0.13 mol.). The reaction mixture was heated to reflux for 12 hours. Acetone (200 mL) was added and the solvent was evaporated. Another 600 mL of acetone were charged to the reaction mixture and it was heated to reflux for 4 to 6 hours. After cooling at 0-5° C., the suspension was filtered and the cake was rinsed twice with acetone (80 mL) to give 49.1 g of Eplerenone. The purity of the Eplerenone obtained at this stage was 99.1%. This material was suspended in 500 ml of methyl ethyl ketone and heated to reflux to give a turbid to clear solution. The solution was filtered hot through cartridge filter. The clear solution was heated to reflux and 175 ml of methyl ethyl ketone were distilled off. The remaining solution (325 mL) was cooled gradually to 0-4° C. and stirred at that temperature for 1 hour. The precipitation was filtered and washed twice with methyl ethyl ketone (50 mL) to provide pharmaceutical grade Eplerenone (recovery=41 g). The product is characterized as follows:

LRMS (APCI+): 415.35 (100.00, $[M+H^+]$)

HRMS ($EI^+$): Calculated for: $C_{24}H_{30}O_6$ $[M]^+$ 414.2042 Found: 414.2050.

$^1$H NMR (DMSO-$d_6$): δ (ppm) 5.98 (1H, s, $H_4$); 3.65 (3H, s, $H_{24}$); 3.13 (1H, d, J =5.3 Hz, $H_{11}$); 2.87-2.90 (1H, m, $H_7$); 2.72 (2H, d, J=2.9 Hz, $H_6$); 2.57-2.66 (1H, m, $H_{21b}$); 2.45-2.54 (4H, m, $H_{2,8,21a}$); 2.27-2.38 (1H, m, $H_{20b}$); 2.17-2.24 (2H, m, $H_{1b,16b}$); 1.83-2.07 (5H, m, $H_{16a,15b,14,12b,20a}$); 1.67-1.73 (1H, dd, J=5.3, 14.6 Hz, $H_{12a}$); 1.47-1.55 (1H, m, $H_{15a}$); 1.49 (3H, s, $H_{19}$); 1.38-1.46 (1H, m, $H_{1a}$); 1.01 (3H, s, $H_{18}$).

$^{13}$C NMR (DMSO-$d_6$): δ (ppm) 198.1, $C_3$; 176.3, C22; 172.7, C23; 165.2, $C_5$; 127.2, $C_4$; 94.7, C17; 65.4, C9; 51.7, C24; 51.6, C11; 44.0, C13; 41.4, C7; 39.8, C10; 38.8, C8; 37.4, C14; 35.1, C16; 34.9, C6; 33.2, C2; 31.0, C12; 31.0, C20; 29.1, C21; 27.1, C1; 22.4, C19; 22.2, C15; 16.3, C18

Example 3

Production of Crude Eplerenone using Methanesulfonyl Chloride and Triethylamine

A mixture of crude Eplerenone (2.00 g, 4.83 mmoL), prepared in a similar manner as the procedure in Example 1, in 10 mL of dichloromethane was treated with triethylamine (48.3 mg, 0.48 mmol.) and methanesulfonyl chloride (55.3 mg, 0.48 mmol.). The reaction mixture was heated to reflux for 12 hours. The solvent was evaporated and to the residue was added acetone (6 mL) whereupon it was heated to reflux for 4 to 6 hours. After cooling at 0-5° C., the suspension was filtered and the cake was rinsed twice with acetone (3 mL) to give 1.10 g of Eplerenone. The purity of the Eplerenone obtained at this stage was 99.2%. This material was further purified by recrystallization from methyl ethyl ketone to provide pharmaceutical grade Eplerenone.

Example 4

Production of Eplerenone using Acetyl Chloride and Triethylamine

A mixture of crude Eplerenone (20.00 g, 48.25 mmol)), prepared in a similar manner as the procedure in Example 1, in 40 mL of dichloromethane was treated with triethylamine (482.6 mg, 48.25 mmol.) and acetyl chloride (3.79 g, 48.25 mmol.). The reaction mixture was heated to reflux for 12 hours. The solvent was evaporated and to the residue was added acetone (40 mL) and it was heated to reflux for 4 to 6 hours. After cooling at 0-5° C., the suspension was filtered and the cake was rinsed twice with acetone (2×16 mL) to furnish 9.30 g of Eplerenone. The purity of the Eplerenone obtained at this stage was 99.0%. This material was further purified by recrystallization from methyl ethyl ketone to provide pharmaceutical grade Eplerenone.

As many changes can be made to the examples which exemplify the invention without departing from the scope of the invention, it is intended that all matter contained herein be considered illustrative of the invention and not in a limiting sense.

The invention claimed is:

1. A process for the preparation of Eplerenone comprising:
(a) epoxidation of trienone IV:

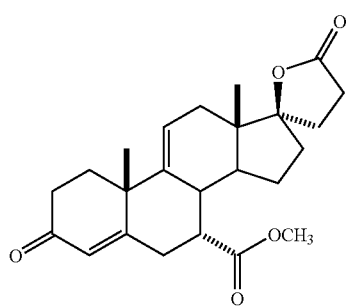

IV with hydrogen peroxide and trichloroacetonitrile in a solvent, thereby forming a reaction mixture;
(b) treatment, in the presence of a base, of the reaction mixture with a derivatizing agent selected from the group consisting of [R'OC(O)]₂, [R'C(O)]₂, R'C(O)X, and R"S(O)₂X, wherein R' is selected from the group consisting of C1 to C6 alkyl, aryl and aralkyl, R" is selected from the group consisting of C1 to C6 alkyl and aryl, and X is a halogen; and
(c) precipitation of Eplerenone.

2. The process of claim 1 wherein the solvent is dichloromethane.

3. The process of claim 1 wherein the derivatizing agent is acetic anhydride and the base is pyridine or collidine.

4. The process of claim 1 wherein the derivatizing agent is acetic anhydride and step (b) is performed in the presence of methyl ethyl ketone.

5. The process of claim 1 where step (b) is performed at about 5° C. to about 50° C.

6. The process of claim 1 where step (b) is performed using about 0.1 equivalents to about 1.0 equivalents of the derivatizing agent.

7. The process of claim 1 wherein the derivatizing agent is selected from the group consisting of [R'OC(O)]₂ or [R'C(O)]₂.

8. The process of claim 1 wherein the derivatizing agent is R'C(O)X.

9. The process of claim 7 wherein R' is methyl.

10. The process of claim 8 wherein X is chloro.

11. The process of claim 8 wherein R' is methyl.

12. The process of claim 11 wherein X is chloro.

13. The process of claim 1 wherein the derivatizing agent is R"S(O)₂X.

14. The process of claim 13 wherein R" is methyl.

15. The process of claim 13 wherein X is chloro.

16. The process of claim 14 wherein X is chloro.

17. A process for the preparation of Eplerenone comprising:
(a) epoxidation of the trienone IV:

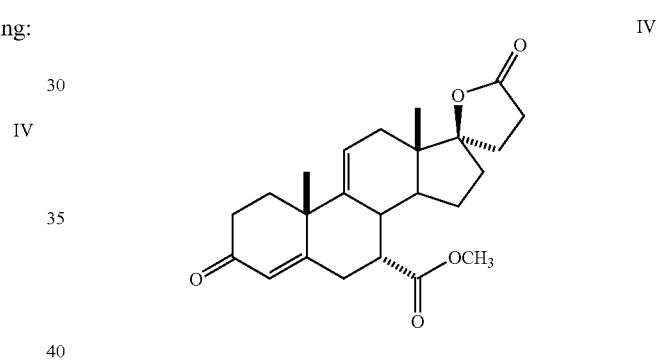

IV with hydrogen peroxide carried out in the presence of trichloroacetonitrile in dichloromethane, thereby forming a reaction mixture;
(b) treatment of the reaction mixture with acetic anhydride carried out in the presence of triethylamine; and
(c) precipitation of Eplerenone.

18. The process of claim 17 where step (b) is performed using about 0.1 equivalents to about 1.0 equivalents of acetic anhydride.

19. The process of claim 17 where step (b) is performed at about 5° C. to about 50° C.

20. The process of claim 1, 2, 3, 4, 5, 6, 7, 8, 9, 10, 13, 11, 17, 19, 18, 12, 14, 15 or 16 further comprising recrystallizing Eplerenone.

21. The process of claim 20 wherein recrystallizing Eplerenone is performed using methyl ethyl ketone.

* * * * *